US00PP12252P2

(12) United States Plant Patent
Lemon

(10) Patent No.: US PP12,252 P2
(45) Date of Patent: Dec. 4, 2001

(54) GERANIUM PLANT NAMED 'SPARKLER RED'

(75) Inventor: David G. Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/478,397

(22) Filed: Jan. 6, 2000

(51) Int. Cl.[7] ..... A01H 5/00
(52) U.S. Cl. ..... Plt./325

(58) Field of Search ..... Plt./325

*Primary Examiner*—Bruce R. Campell
*Assistant Examiner*—A Para
(74) *Attorney, Agent, or Firm*—Webb Ziesenheim Logsdon Orkin & Hanson, P.C.

(57) ABSTRACT

A new and distinct cultivar of geranium characterized by varying degrees of colors including candy pink, bright red, coral, pale pink, and white. The unpredictable streaking and spotting of these colors makes each floret unique. This variety exhibits improved cutting production, rooting speed and stock plant growth.

1 Drawing Sheet

BACKGROUND OF THE INVENTION

This discovery relates to a new and distinct cultivar of geranium identified by the name of 'Sparkler Red', Breeder No. 5DG2388 and Oglevee, Ltd. No. 6142. The new variety was discovered in a selective breeding program at Oglevee, Ltd. in Connellsville, Pa. The new variety was first asexually reproduced on Jan. 27, 1997 in Connellsville, Pa. and has been found to retain its distinctive characteristics through successive generations.

The 'Sparkler Red' variety is characterized by its multi-patterned double florets that are variations of red, white, and pink in coloration. This coloration is presented in streaks, spots, and patches of varying size. This variety is best compared with the Geo. J. Ball, Inc. variety 'Starburst Red' (U.S. Plant Pat. No. 9,229) which, likewise, has multi-patterned florets, albeit of the single type. The new cultivar is not prone to whole petals of solid color as is the case for the 'Starburst Red' variety. The plant was propagated asexually by cutting.

The new cultivar, when grown in a glass greenhouse in Connellsville, Pa. using full light, 60° F. night temperature, 68° F. day temperature and grown in a soilless media with constant fertilizer at 200–250 ppm nitrogen and potassium with full light, has a response time from a rooted cutting to a flowering plant in a 10 cm pot of six weeks. The time to produce a root cutting is 21 to 25 days.

DESCRIPTION OF THE DRAWING

The accompanying photographic drawing illustrates the new cultivar 8 weeks from root cutting, with the color being as nearly true as is possible with color illustrations of this type.

DESCRIPTION OF THE PLANT

The following detailed descriptions set forth the characteristics of the new cultivar. The data which define these characteristics were collected from asexual reproductions carried out at Oglevee, Ltd., 152 Oglevee Lane, Connellsville, Pa. 15425. The color readings on a plant grown in a 10 cm pot were taken indoors under 200–220 foot candles of cool white fluorescent light. Color references are to the R.H.S. Colour Chart of The Royal Horticultural Society of London and common color names.

THE PLANT

Classification:
- *Botanical.*—*Pelargonium xhortorum.*
- *Commercial.*—Geranium named 'Sparkler Red'.

Form: Uniform mound.
Height: 26.0–28.5 cm.
Growth: Free basal branching.
Strength: Needs no artificial support, flowers supported on strong stems.
Foliage: Stalked leaf attachment.
Leaves:
- *Size.*—6.5–10.2 cm across.
- *Shape.*—Reniform; cordate base.
- *Margin.*—Crenate.
- *Texture.*—Smooth, pubescent, slightly reflective.
- *Arrangement.*—Alternate, sometimes opposite.
- *Color.*—Top: Green Group 137A. Bottom: Green Group 137D. Zone: None observed.
- *Ribs and veins.*—Venation: Palmate. Color: Yellow-Green Group 144A.

Petioles:
- *Length.*—5.2–10.5 cm.
- *Color.*—Yellow-Green Group 144A.
- *Texture.*—Pubescent.

Stem:
- *Color.*—Yellow-Green Group 144A.
- *Internode length.*—3.0–4.2 cm.
- *Texture.*—Pubescent.

THE BUD

Shape of cluster: Elliptical.
Size:
- *Umbel.*—4.0–5.0 cm across when bud just showing color.
- *Bud.*—1.0–1.4 cm long; 0.6–0.9 cm wide, when just showing color.

Sepals: A ring of 5 to 6 sepals present; texture is pubescent; size is 3 to 5 mm wide and 7 to9 mm long; color is Yellow-Green Group 144A changing to Greyed-Red Group 178B at the base.

INFLORESCENCE

Blooming habit: Continuous, free and early flowering; semi-double flowers. Blooming period is 12 to 14 days, and the duration of the bloom is approximately 7 days.

Borne: Umbel, florets on pedicel, pedicel on peduncle.

Open florets:

*Form.*—Ruffled, slightly cupped to cupped.

*Size of fully open bloom.*—8.0–10.5 cm across umbel.

*Color.*—Upper side of florets: Florets are a variety of colors. Some are red, some are pink, some are a mixture of each. Colors in the pink florets are: Red-Purple Group 62A at outer edge fading to a Red-Purple Group 62C toward center with a coral-pink Red Group 52D near base of petal. Some petals are lighter, almost white in center with the darker pink around the edge and veining of Red Group 52B. Colors in the red florets include: Red Groups 45A and 45B and Red Group 43D toward the base with some having streaks of Red Group 44A. The base of the petal is white. Veining of Red Group 47A. Florets with mixtures of red and pink have irregular streaking and spotting patterns of Red Groups 46A and 46B, Red Group 47A, Red Groups 45A and 45B, Red Group 55B, Red Group 55C, Red Groups 54A and 54B and Red Group 48A. Underside of florets: Pink florets have Red-Purple Group 62B at outer edge fading into a Red-Purple Group 62D. Red florets are Red Group 47A at outer edge fading to Red Groups 44A and 44B toward center. Base of petal is white. The mixed florets have varying degrees of the pink and red shades as on top surface of petals. Eye: None.

*Petals.*—Quantity: 9–11. Size: 1.3–1.7 cm wide; 1.9–2.5 cm long.

Texture and appearance: Highly reflective, smooth, velvety; appearance from a distance is a unique coral pink and rose above medium green foliage.

Petaloids:

*Quantity.*—0–3.

*Shape.*—Irregular; twisted; some with cut edges, some tubular in shape.

*Color.*—Same as petals.

Pedicel:

*Length.*—2.5–3.5 cm.

*Color.*—Yellow-Green Group 144B with Greyed-Purple Group 185A.

*Texture.*—Pubescent.

Peduncle:

*Length.*—14.0–22.0 cm.

*Color.*—Yellow-Green Group 144A.

Texture: Pubescent.

Disease resistance: Not known.

Lasting quality: This variety holds up well under outdoor conditions, both high temperatures and rainy conditions. The bloom returns quickly after rain. Flowers hold for 7–14 days depending on conditions, new continuously replacing the old.

Flower fragrance: None.

REPRODUCTIVE ORGANS

Stamens:

*Number.*—6 to 8.

*Anthers.*—2.0 mm long. Filaments: Length: 7.0–8.1 cm. Color: White Group 155B. Pollen color: Orange-Red Group 34A.

*Pistils.*—Number: 1. Length: 8.0–9.5 cm. Stigma color: Red Group 53A. Style: 3.0–3.5 cm long. Ovaries: Yellow-Green Group 148D; pubescent; superior; 5.5–6.0 mm long.

Fruit: None observed.

Seed: Not produced.

GENERAL CHARACTERISTICS

'Sparkler Red' is characterized by double florets having coloration varying from bright red through pale pink to white presenting as streaks, spots, and patches of varying size. The unpredictable but always present streaking and spotting of these colors makes each floret unique. These color characteristics are common with 'Starburst Red' although a solid color petal rarely occurs. Cutting production, rooting speed, and stock plant growth are all more controlled and improved over 'Starburst Red'. The foliage color is also a deeper green, giving a better color contrast between bloom and foliage.

I claim:

1. A new and distinct cultivar of geranium plant named 'Sparkler Red' as described and illustrated herein.

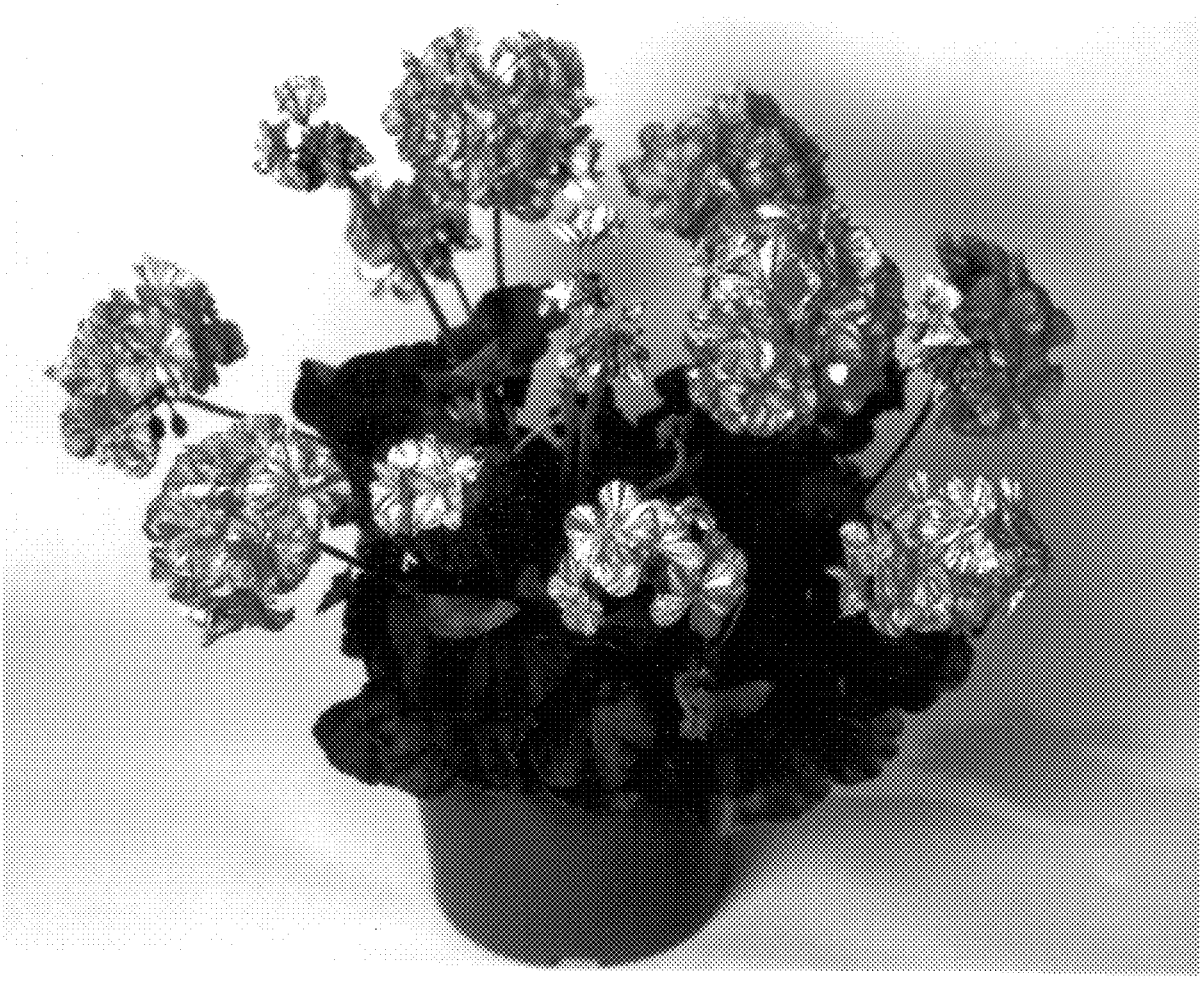

* * * * *